US012751641B2

(12) United States Patent
Wang

(10) Patent No.: US 12,751,641 B2
(45) Date of Patent: Oct. 6, 2026

(54) MEASURING DEVICE FOR MEASURING CARDIOPULMONARY STATE

(71) Applicant: NATIONAL TSING HUA UNIVERSITY, Hsinchu City (TW)

(72) Inventor: Ting-Wei Wang, Hsinchu City (TW)

(73) Assignee: NATIONAL TSING HUA UNIVERSITY, Hsinchu City (TW)

( * ) Notice: Subject to any disclaimer, the term of this patent is extended or adjusted under 35 U.S.C. 154(b) by 327 days.

(21) Appl. No.: 18/594,143

(22) Filed: Mar. 4, 2024

(65) Prior Publication Data

US 2024/0350025 A1 Oct. 24, 2024

(30) Foreign Application Priority Data

Apr. 24, 2023 (TW) ................................ 112115147

(51) Int. Cl.

| | |
|---|---|
| ***A61B 5/053*** | (2021.01) |
| ***A61B 5/00*** | (2006.01) |
| ***A61B 5/0205*** | (2006.01) |
| ***A61B 5/025*** | (2006.01) |
| ***A61B 5/08*** | (2006.01) |
| *A61B 5/085* | (2006.01) |

(52) U.S. Cl.

CPC ............ *A61B 5/053* (2013.01); *A61B 5/0205* (2013.01); *A61B 5/725* (2013.01); *A61B 5/086* (2025.01)

(58) Field of Classification Search

CPC ....... A61B 5/0205; A61B 5/053; A61B 5/086; A61B 5/725

See application file for complete search history.

(56) References Cited

U.S. PATENT DOCUMENTS

| | | | |
|---|---|---|---|
| 8,652,040 | B2 | 2/2014 | LeBoeuf et al. |
| 10,806,352 | B2 | 10/2020 | Sweeney et al. |
| 10,905,393 | B2 | 2/2021 | Gifford, III et al. |
| 11,092,685 | B2 | 8/2021 | Shouldice et al. |

(Continued)

FOREIGN PATENT DOCUMENTS

| | | | |
|---|---|---|---|
| CN | 107405083 | A | 11/2017 |
| CN | 108474841 | A | 8/2018 |

(Continued)

*Primary Examiner* — Scott Luan

(74) *Attorney, Agent, or Firm* — Birch, Stewart, Kolasch & Birch, LLP

(57) ABSTRACT

A measuring device for measuring cardiopulmonary state comprises a sensor and a control module. The sensor comprises a substrate and a coil arranged on the substrate. The coil is configured to transmit a first electromagnetic signal towards the part to be measured, and receive at least a second electromagnetic signal generated by the induction of the first electromagnetic signal to generate an induction signal. The control module is coupled to the coil. The control module includes a signal generating unit configured to provide an AC signal to the coil, a filtering unit coupled to the coil, and a processing unit. The filtering unit has at least a first filtering frequency band and a second filtering frequency band. The induction signal is divided into at least a first part and a second part aft"r pa’sing through the filtering unit. The processing unit calculates at least one feature signals of the state of the subject’s heart or lungs according to at least one of the first part and the second part.

11 Claims, 11 Drawing Sheets

(56) References Cited

U.S. PATENT DOCUMENTS

| | | | | |
|---|---|---|---|---|
| 11,517,283 | B2 | 12/2022 | Leijssen et al. | |
| 2003/0187341 | A1* | 10/2003 | Sackner | A61B 5/6804 600/388 |
| 2008/0065181 | A1 | 3/2008 | Stevenson | |
| 2018/0059059 | A1 | 3/2018 | Sarhan et al. | |
| 2019/0343417 | A1* | 11/2019 | Leijssen | A61B 5/243 |
| 2020/0082926 | A1 | 3/2020 | Tai et al. | |
| 2020/0170527 | A1 | 6/2020 | Kale et al. | |
| 2022/0071502 | A1 | 3/2022 | Peeters et al. | |

FOREIGN PATENT DOCUMENTS

| | | | |
|---|---|---|---|
| CN | 108879995 | A | 11/2018 |
| CN | 110300546 | A | 10/2019 |
| CN | 113453616 | A | 9/2021 |
| CN | 113598745 | A | 11/2021 |
| CN | 114631797 | A | 6/2022 |
| EP | 2 062 525 | A2 | 5/2009 |
| JP | 2015-208451 | A | 11/2015 |
| JP | 2020-513929 | A | 5/2020 |

* cited by examiner

MEASURING DEVICE FOR MEASURING CARDIOPULMONARY STATE

TECHNICAL FIELD

The present invention relates to a measuring device, in particular, to a card-type, non-invasive measuring device for measuring cardiopulmonary state using magnetoelectric effect.

BACKGROUND

The state of the heart or lungs of a subject is a key indicator in long-distance care or home care. To meet the needs of measurement or detection, a subject must wear sensor(s) or detector(s) for a long time to allow the caregiver to track the subject's cardiopulmonary state. If a subject needs to wear a sensor for a long time, the comfort of the subject wearing the sensor should be considered so that the subject's physical or mental health will not be affected.

However, conventional non-contact measuring mechanisms cannot easily meet the requirements mentioned above. For example, optical plethysmography (PPG), due to its mechanism of optical penetration/reflection, can be easily affected by external factors such as the subject's clothing and/or skin. On the other hand, conventional magnetoelectric electric effect sensing methods cannot provide a better way to wear the sensing device. Specifically, the coil or other components of a magnetoelectric electric effect sensing device can easily affect the daily life of the subject, e.g., causing discomfort or difficulty in movement. In addition, because the to-be-testedtarget to be tested by the cardiopulmonary state-sensing device is the heart or lungs of the subject, which are adjacent to each other and positioned at similar positions/depths in the subject's body, the measured signals are prone to interaction and interference with each other, which affects the measurement accuracy and ease of interpretation.

Therefore, providing a non-contact and less burdensome measurement mechanism for the subject while meeting the needs of monitoring the state of the subject's heart or lungs will be a key issue in this field.

SUMMARY

An object of the present invention is to provide a non-invasive measuring device for measuring cardiopulmonary state which can be stably worn.

An object of the present invention is to provide a non-invasive measuring device for measuring cardiopulmonary state which can eliminate or reduce interference between the signals from heart and lungs.

The present invention provides a measuring device for measuring cardiopulmonary state. The device comprises a sensor and a control module. The sensor includes a substrate and a coil arranged on the substrate. Wherein the coil is configured to transmit a first electromagnetic signal toward a to-be-measured part of a subject and receive at least a second electromagnetic signal induced by the first electromagnetic signal and generated at the to-be-measured part. Wherein the second electromagnetic signal is converted to a sensing signal by the coil. The control module includes a signal generation unit coupled to the coil, a filter unit coupled to the coil, and a processing unit coupled to the filter unit. Wherein the signal generating unit is configured to generate an AC signal to be provided to the coil to generate the first electromagnetic signal. Wherein the filter unit has at least a first filter frequency band and a second filter frequency band. Wherein the sensing signal is filtered by the filter unit to have at least a first portion corresponding to the first filter frequency band, and a second portion corresponding to the second filter frequency band. Wherein the processing unit is configured to calculate, based on the first portion and/or the second portion, at least one feature signal of the subject's cardiopulmonary state.

As mentioned above, the measuring device for measuring cardiopulmonary state provided by the present invention is arranged on a substrate and can be easily worn on the subject's chest. For example, a card-type sensor can be placed in a chest pocket of the subject or attached to the subject's chest. In addition, the feature signals of the heart and the lungs of the subject can be distinguished by the filter unit. Hence, the measuring device will eliminate or reduce signal interference caused by interaction of the signals from the heart and lungs.

BRIEF DESCRIPTION OF THE DRAWINGS

The accompanying drawings are presented to help describe various aspects of the present invention. In order to simplify the accompanying drawings and highlight the contents to be presented in the accompanying drawings, conventional structures or elements in the accompanying drawings may be drawn in a simple schematic way or may be omitted. For example, the number of elements may be singular or plural. These accompanying drawings are provided merely to explain the embodiments and not to limit them.

DETAILED DESCRIPTION

Figure 1:
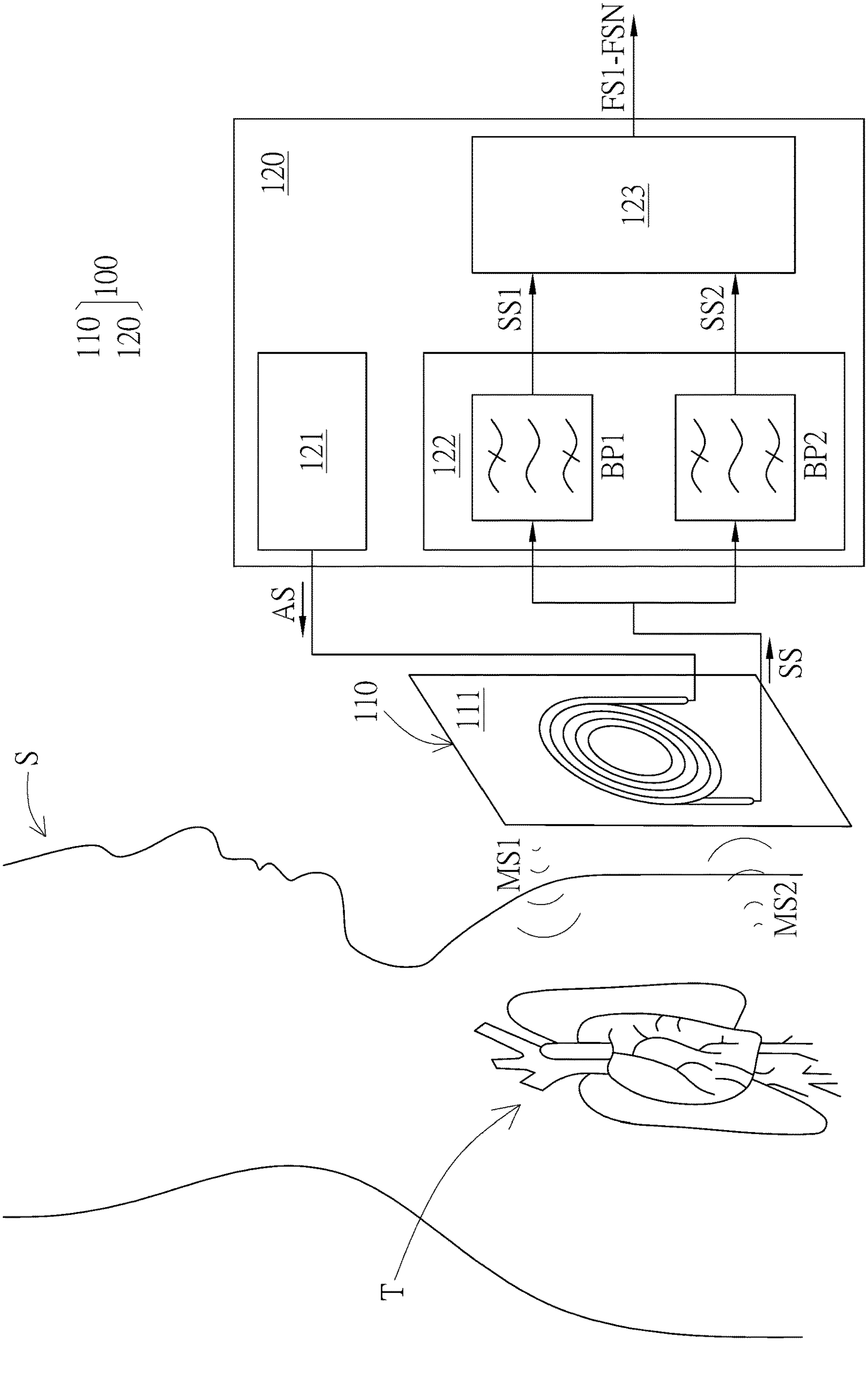
FIG. 1 is a schematic diagram of the measuring device for measuring cardiopulmonary state according to the first embodiment of the present invention.
Figure 2:
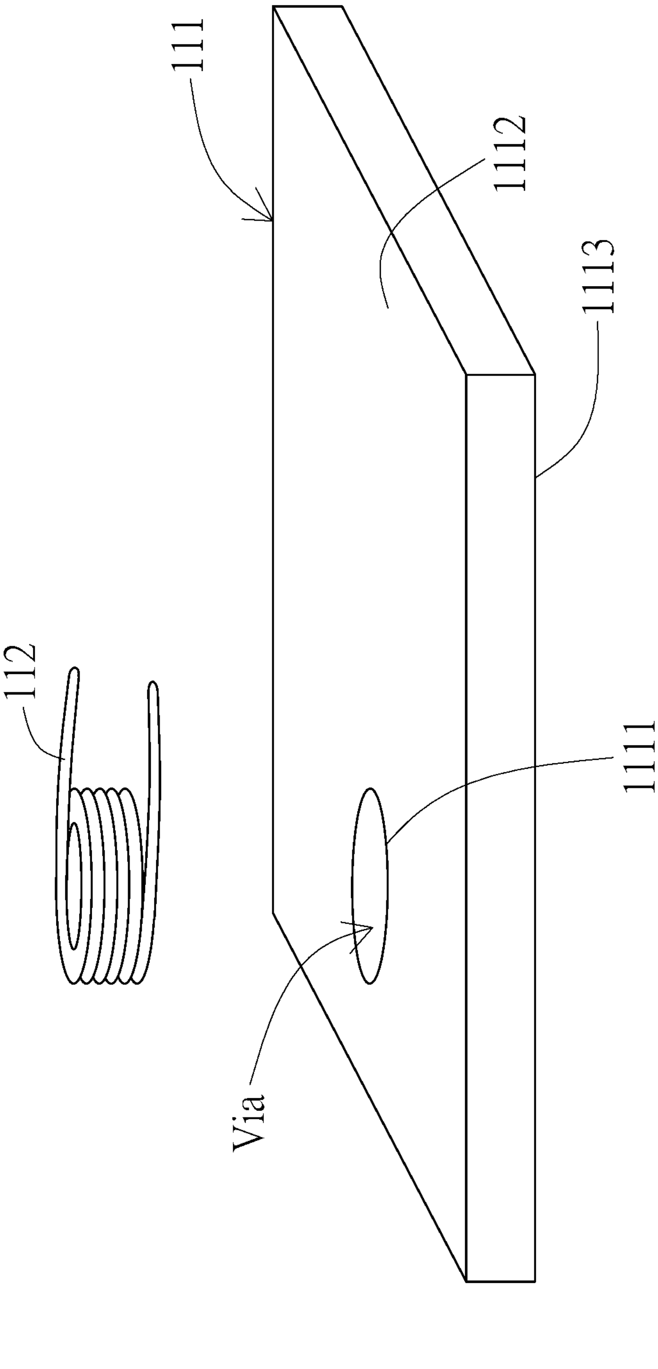
FIG. 2 is a schematic diagram of the coil arranged on a substrate according to the first embodiment of the present invention.
Figure 3:
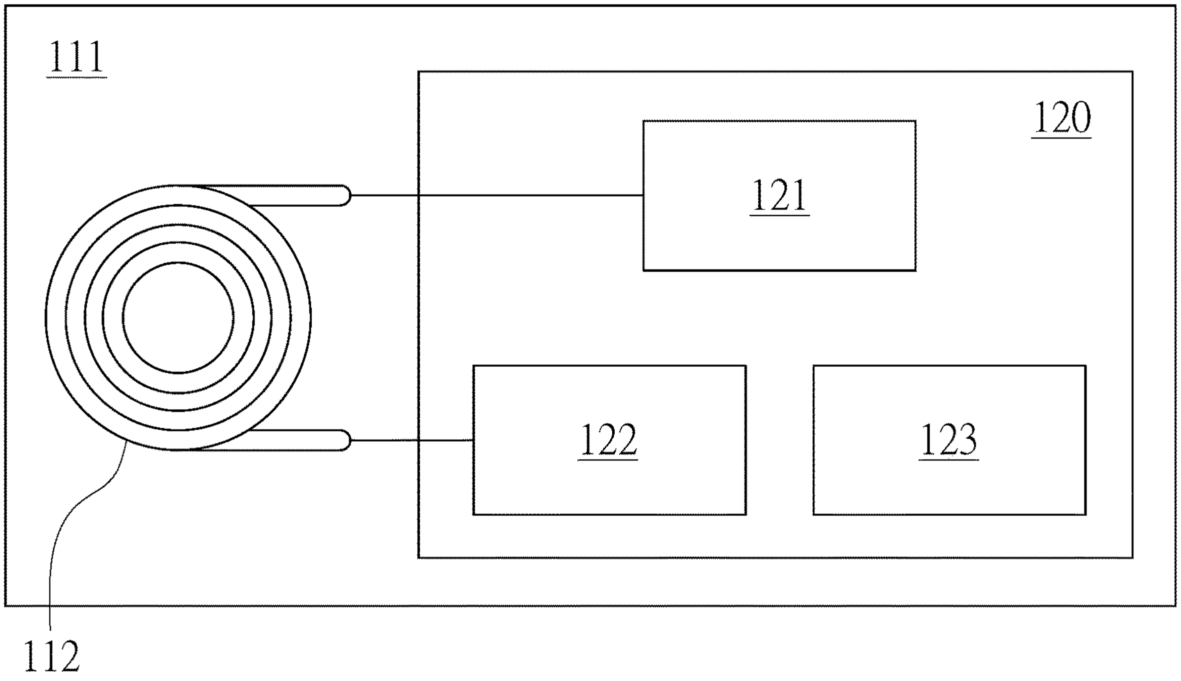
FIG. 3 is a block diagram of the control module integrated on a substrate according to the first embodiment of the present invention.

Any reference to elements using terms such as "first" and "second" herein generally does not limit the number or order of these elements. Conversely, these names are used herein as a convenient way to distinguish two or more elements or element instances. Therefore, it should be understood that the terms "first" and "second" in the request item do not necessarily correspond to the same names in the written description. Furthermore, it should be understood that references to the first element and the second element do not indicate that only two elements can be used or that the first element needs to precede the second element. Open terms such as "include", "comprise", "have", "contain", and the like used herein means including but not limited to.

The term "coupled" is used herein to refer to direct or indirect electrical coupling between two structures. For example, in an example of indirect electrical coupling, one structure may be coupled with another structure through a passive element such as a resistor, a capacitor, or an inductor.

In the present invention, the term such as "exemplary" or "for example" is used to represent "giving an example, instance, or description". Any implementation or aspect described herein as "exemplary" or "for example" is not necessarily to be construed as preferred or advantageous over other aspects of the present invention. The terms "about" and "approximately" as used herein with respect to a specified value or characteristic are intended to mean within a value (for example, 10%) of the specified value or characteristic.

In the present invention, the term "cardiac state" referred to herein is, but not limited to, a state of medical or non-medical significance such as cardiac contraction and/or relaxation, pulse, cardiac elasticity, valve opening and closing, state of cardiac wall, etc. The term "pulmonary state" referred to herein is, but not limited to, a state of medical or non-medical significance such as respiratory rate, dilation, collapse, etc.

First Embodiment

Refer to FIG. 1 to FIG. 5. The first embodiment discloses the measuring device 100 for measuring cardiopulmonary state. The measuring device 100 comprises a sensor 110 and a control module 120. The sensor 110 includes a substrate 111 and a coil 112 arranged on the substrate 111. The coil 112 is configured to transmit a first electromagnetic signal MS1 toward the to-be-measured part T of the subject S, and receive at least a second electromagnetic signal MS2 induced by the first electromagnetic signal MS1 and generated at the to-be-measured part T, wherein the second electromagnetic signal MS 2 is converted to a sensing signal SS by the coil. The control module 120 includes a signal generation unit 121 coupled to the coil 112, a filter unit 122 coupled to the coil 112, and a processing unit 123 coupled to the filter unit 122. The signal generation unit 121 is configured to generate an AC signal AS to be provided to the coil 112 to generate the first electromagnetic signal MS1. The filter unit 122 coupled to the coil 112 has at least a first filter frequency band BP1 and a second filter frequency band BP2. The sensing signal SS is filtered by the filter unit 122 to have a first portion SS1 corresponding to the first filter frequency band BP1 and a second portion SS2 corresponding to the second filter frequency band BP2. The processing unit 123 is configured to calculate, based on the first portion SS1 and/or the second portion SS2, at least one feature signal FS1-FSN of the subject's cardiopulmonary state.

The sensor 110 includes the substrate 111. The material of the substrate 111 may be a hard material with carrying capacity such as glass fiber or silicon, or a soft/flexible material such as polyimide or polyester resin. More specifically, a substrate 111 made by hard material may provide better mechanical strength and avoid damage to the coil 112. On the other hand, a substrate 111 made by soft/flexible material may have flexibility and/or bendability, which will provide a comfortable or fitting wearing experience. The sensor 110 is preferably fabricated in a card size (e.g. 8-10 cm in length and 5-7 cm in width) for ease of placement in a front pocket on the chest of a subject S. However, the size of sensor 110 is not limited thereto.

The coil 112 of the sensor 110 can be a trace formed on the substrate 111. More specifically, conducting wire(s) can be formed on substrate 111 by using conventional manufacturing techniques such as etching, engraving, and lithography. The conducting wire has at least one radiating portion to emit the first electrical signal MS1 and receive the second electrical signal MS2. The present invention is not limited to any formation/type of the coil 112. The coil 112 may be, for example, a single-turn coil, a multi-turn coil, or a spiral coil, but not limited thereto. In addition, the coil 112 can be formed as a planar coil, for example, a planar coil made by a conducting wire on a layer of the substrate 111. On the other hand, the coil 112 can also be made as a three-dimensional coil, for example, a coil made by a conducting wire on two or more layers of the substrate 111. It should be noted that each part of the coil 112 distributed in different layers can be electrically coupled, for example, through conductive holes connecting the layers of the substrate 111. In this way, the coil 112 and the substrate 111 can be produced using conventional circuit manufacturing methods, which can effectively improve the yield and consistency of the production of the sensor 110.

However, the coil 112 may also be an individual component arranged on the substrate 111. For example, the coil 112 may be a coil wound by an enameled wire (for example only, not to limit the material of the coil) arranged on the substrate 111 by adhesive or other setting means. In the embodiment, the present invention is not limited in regard to the thickness of the substrate 111. More specifically, referring to FIG. 2, the substrate 111 can have a setting area 1111, and the coil 112 can be set within the setting area 1111 of the substrate 111. Preferably, the depth (thickness) of the setting area 1111 is equal to or slightly longer than the height/thickness of the coil 112. Therefore, when setting the coil 112 into the setting area 1111, the coil 112 will not protrude from the surface 1112 of the substrate 111. In the embodiment, the depth of the setting area 1111 may be equal to the thickness of the substrate 111. In other words, the setting area 1111 is a through-hole (via) that connects the surface 1112 to the surface 1113 of the substrate 111, and the coil 112 is arranged in the through-hole (via). By using an individual component as the coil 112, people may select different types of coils with different radiation parts, such as coils of different materials, turns, and shapes according to the purpose or application. In addition, for measurement accuracy, the individual coil 112 can also be replaceable or disposable, which has more flexibility in applications.

The control module 120 is coupled to the coil 112 of the sensor 110. For example, the control module 120 may be an independent module coupled to the coil 112. More specifically, the independent control module 120 can be a module or a device having programmable or instrument-controlling capability such as a computer, a tablet computer, an industrial computer, an instrument, FPGA, microprocessor, etc. By using an independent module or device as the control module 120, one may select, according to the needs, a control module 120 of different computing capabilities to meet different requirements. For example, the control module 120 may be a high-performance or advanced control module for high computing power or regulatory/safety requirements. On the contrary, for applications requiring lightweight and ease of carrying, the processing unit 123 of the control module 120 may be made of integrated circuits such as system on chip (SOC) or application specific integrated circuit (ASIC).

On the other hand, the control module 120 can also be integrated with the sensor 110 and coupled with the coil 112. More specifically, referring to FIG. 3, the control module 120 can be arranged on the substrate 111. For example, conducting wires (traces) and setting pads can be formed on the surface of the substrate 111 and configured to connect the required active/passive components for the control module 120. The means for arranging the required active/passive components for the control module 120 on the substrate 111 can be, for example, welding or other conventional workmanship. In this way, the sensor 110 and the control module 120 can be integrated into a card-type device or a device with a shell. This can improve the overall integrity of the measuring device 100 for measuring cardiovascular state and enhance the convenience of wearing.

Figure 4:
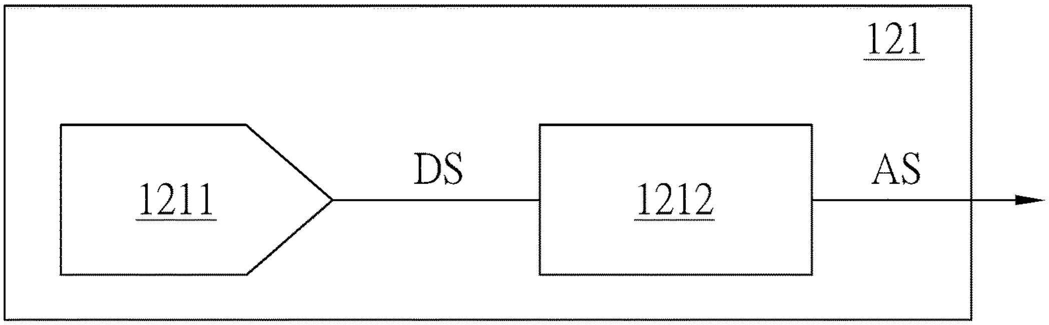
FIG. 4 is a block diagram of the signal generation unit according to the first embodiment of the present invention.

The signal generation unit 121 can be an AC/DC signal generation unit composed of active components (such as oscillators or timers) and/or passive components (such as resistors, capacitors, or inductors). More specifically, the signal generation unit 121 may directly generate an AC signal (AC) by the circuit composed of active/passive components. On the other hand, the signal generation unit 121 may be configured to convert DC signals into AC signals (AC) through the circuit composed of active/passive components. For example, as shown in FIG. 4, the signal generation unit 121 includes a DC power supplier 1211 and a resonant circuit 1212 receiving the DC signal (DS) provided by the DC power supplier 1211 to generate the AC signal (AS). By using the DC power supplier 1211 and the resonant circuit 1212, the AC signal (AS) can be generated by the resonant circuit 1212 by only requiring a combination of passive components (such as the resistor (R), the capacitor (C), and the inductor (L)) in series or parallel. Therefore, the signal generation unit 121 shown in FIG. 4 will provide effects such as simplifying the circuit and lowering energy consumption. In the embodiment, the resonant frequency range of the resonant circuit 1212 is preferably 1-10 MHz to correspond to the depth of the heart/lungs and achieve lower eddy current damping.

Figure 5:
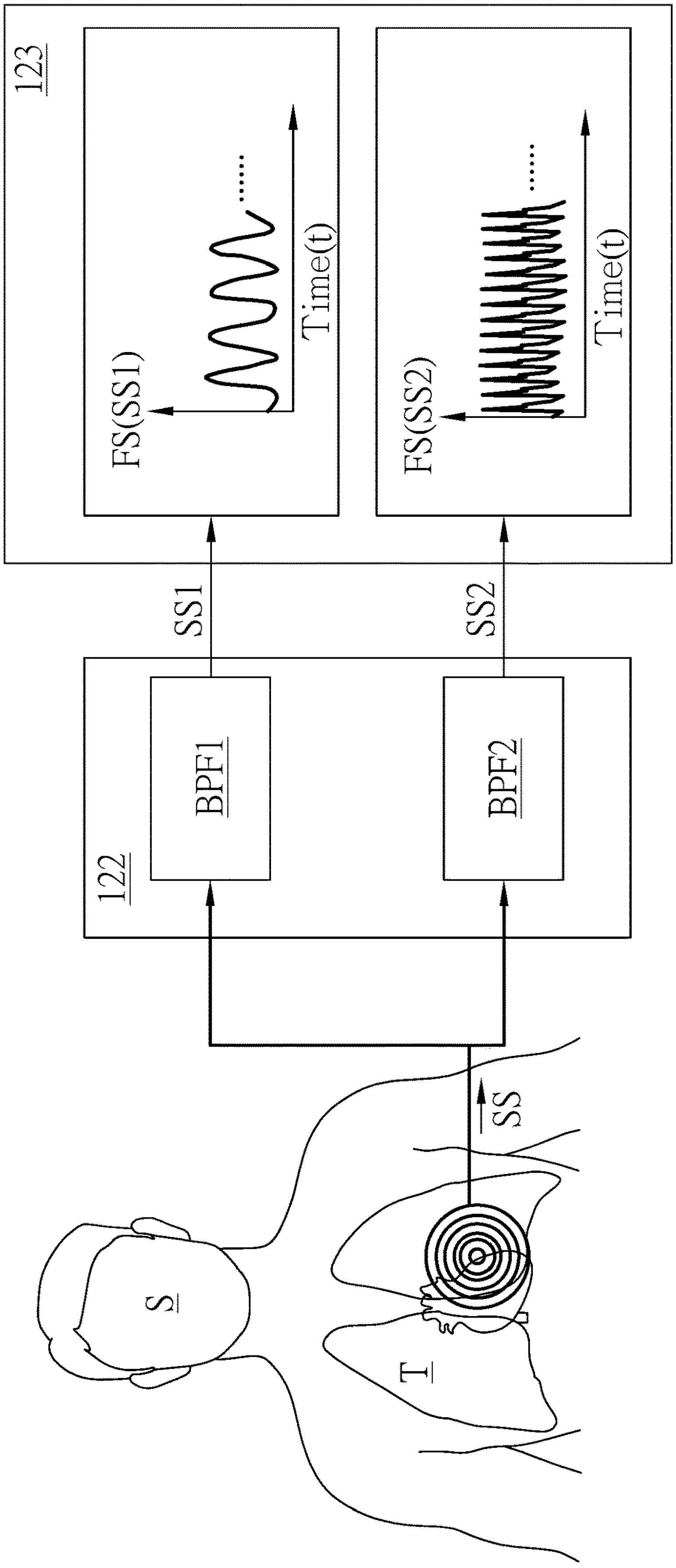
FIG. 5 is a block diagram of the filter unit according to the first embodiment of the present invention.

Referring to FIG. 5, the signal generation unit 121 is configured to provide the AC signal AS to the coil 112, and the coil 112 generates the first electromagnetic signal MS1 due to electromagnetic effect. The coil 112 is configured to output the first electromagnetic signal MS1 to the to-be-measured part T to generate an eddy current at the to-be-measured part T. More specifically, after the first electromagnetic signal MS1 is applied to the to-be-measured part T, the tissues, blood vessels, or blood of the heart and/or lungs at the to-be-measured part T may be regarded as a conducting plane, which may generate the eddy current I correspondingly due to the first electromagnetic signal MS1. Hence, the eddy current may generate the second electromagnetic signal MS2. The parameter(s) of the eddy current (such as amplitude, direction, or frequency) will vary with the state of the heart and/or lungs at the to-be-measured part T. The eddy current will generate the second electromagnetic signal MS2 in a direction opposite to the magnetic field direction of the first electromagnetic signal MS1. The second electromagnetic signal MS2 will then be received by the coil 112. In other words, the second electromagnetic signal MS2 (by itself or after interacting with the first electromagnetic signal MS1 and/or other signals) will generate a magnetoelectric effect on the coil 112 and thus generate an induced sensing signal (SS).

The filter unit 122 has at least the first filter frequency band BP1 and the second filter frequency band BP2. The sensing signal SS is filtered by the filter unit 122 to be divided into, at least, the first portion SS1 corresponding to the first filter frequency band BP1 and the second portion SS2 corresponding to the second filter frequency band BP2. Usually, respiratory rate varies with the subject's age, gender, or physiological state. For example, for an adult, the respiratory rate may be 12-20 times per minute in normal state. But if the subject is exercising or is an infant, the respiratory rate may be 40-60 times per minute. Therefore, one may choose an appropriate frequency between 0.2 and 1 Hz as the first filter frequency band BP1 according to the needs. On the other hand, heart rate also varies with the subject's age, gender, or physiological state. For example, the heart rate of an adult may be 60-100 beats per minute in normal state. But if the subject is exercising, or in an abnormal state, or is an infant or young children, the heart rate may be 130-150 beats per minute. Therefore, one may choose an appropriate frequency between 0.5 and 2.5 Hz as the second filter frequency band BP2 according to the needs. It should be noted that, a skilled person in the field can choose other frequencies as the first filter frequency band BP1 and/or the second filter frequency band BP2 based on other lungs or heart states. The present invention is not limited to the frequency examples mentioned in above embodiments. The filter unit 122, for example, includes the first bandpass filter BPF1 and the second bandpass filter BPF2. The passband of the first bandpass filter BPF1 corresponds to the first filter frequency band BP1, and the passband of the second bandpass filter BPF2 corresponds to the second filter frequency band BP2. More specifically, the first filter frequency band BP1 may correspond to the frequency of the lung state signal (such as the frequency of expansion and contraction of the lungs during breathing). The second filter frequency band BP2 may correspond to the frequency of the heart state signal (such as the frequency of heart beat or pulse). Preferably, the first filter frequency band BP1 is at least partially lower than the second filter frequency band BP2.

The processing unit 123 is configured to calculate at least one feature signal FS1-FSN of the heart or lung state of the subject S at the to-be-tested part T based on at least one of the first portion SS1 and the second portion SS2. For example, the processing unit 123 calculates the feature signal FS (SS1) of the lung state of the subject S based on the first portion SS1 (the lower frequency portion of the sensing signal) and/or the feature signal FS(SS2) of the heart state of the subject S based on the second portion SS2 (the higher frequency portion of the sensing signal).

Second Embodiment

Figure 6:
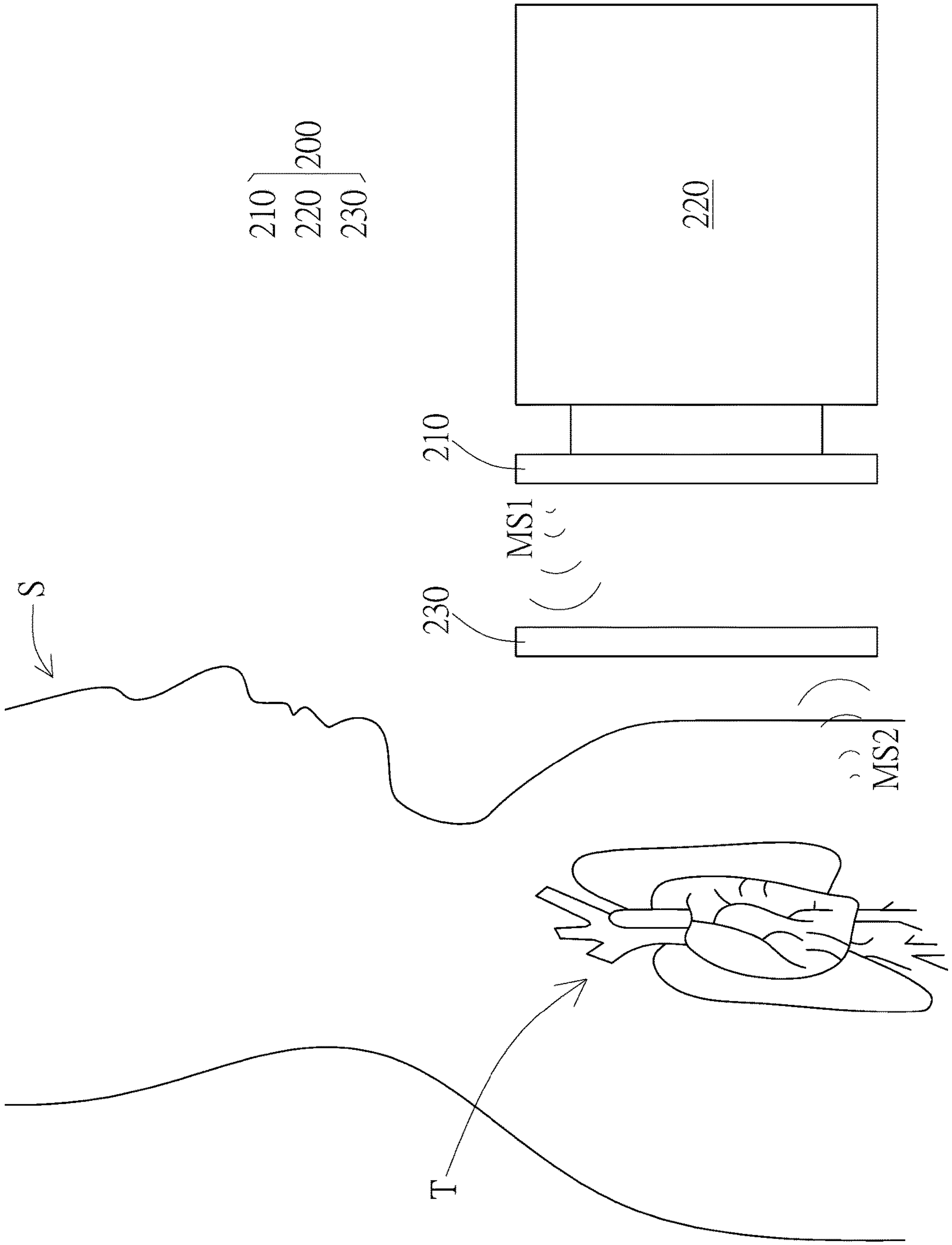
FIG. 6 is a schematic diagram of the measuring device having a matching element for measuring cardiopulmonary state according to the second embodiment of the present invention.

In the second embodiment, referring to FIG. 6, the measuring device 200 for measuring the cardiovascular state may further include a matching element 230. The matching element 230 is arranged between the sensor 210 and the subject S. More specifically, the matching element 230 may be made of materials with magnetic impedance between the magnetic impedance of the subject S and the magnetic impedance of the sensor 210. Accordingly, the matching element 230 may reduce energy loss during the energy transfer between the first electrical signal MS1 and the second electrical signal MS2 and achieve the goals of measuring the required signal and improving the signal-to-noise ratio with lower energy, so that issues such as injuring the subject S with excessive energy or low endurance of the measuring device may be avoided. On the other hand, the matching element 230 can also serve as a contact buffer between the sensor 210 and the subject S. For example, the matching element 230 may improve the comfort of the subject S or the stability of the measuring device during measurement. However, the purpose of installing the matching element 230 is not limited to the above examples.

Third Embodiment

Figure 7:
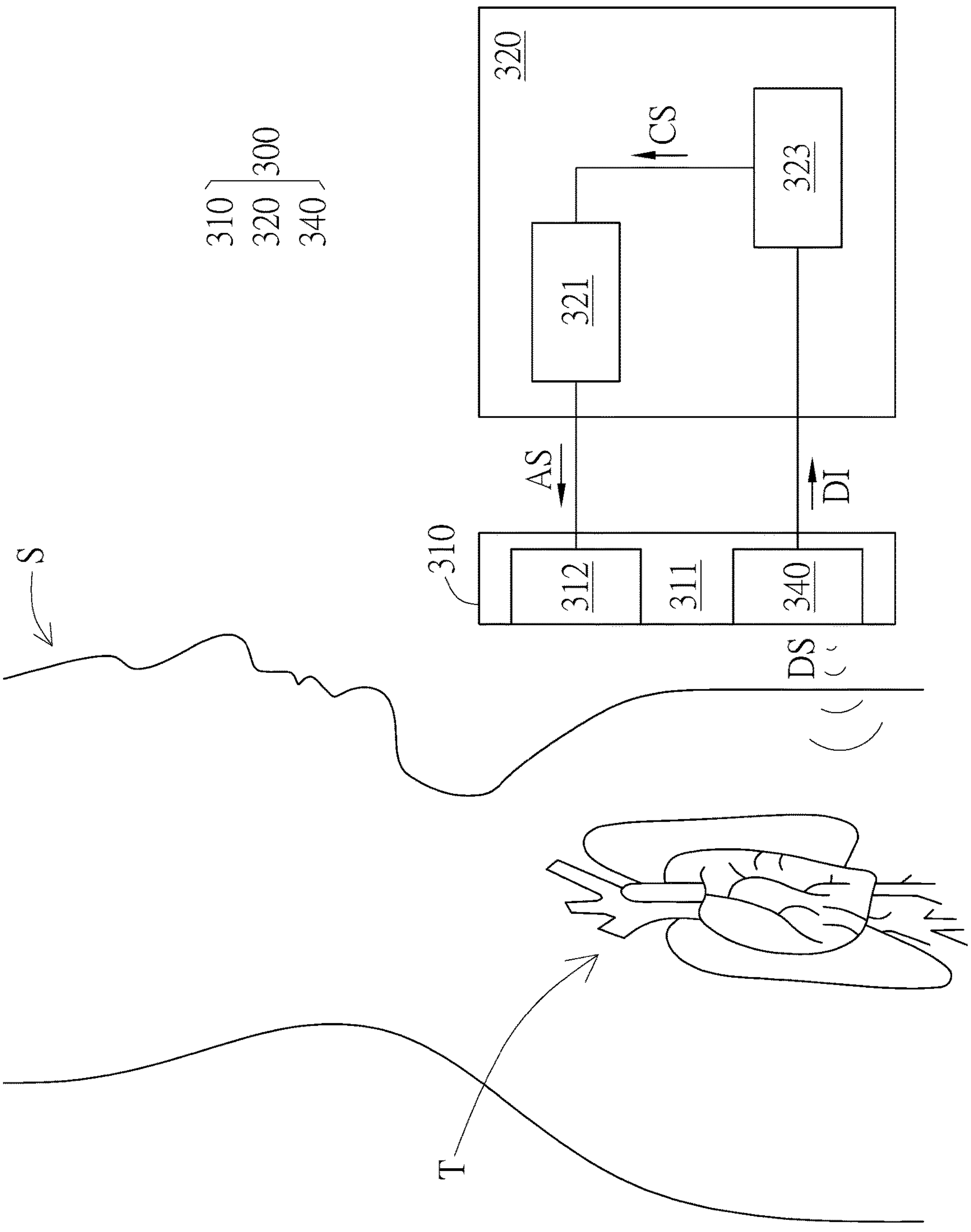
FIG. 7 is a schematic diagram of the measuring device having a depth detection unit for measuring cardiopulmonary state according to the third embodiment of the present invention.

In this embodiment, referring to FIG. 7, the measuring device 300 for measuring cardiovascular state further includes a depth detection unit 340. The depth detection unit 340 is configured to send a detection signal DS to the to-be-measured part T and provide the depth information DI corresponding to the heart or lungs of the subject S to the control module 320. The control module 320 adjusts the frequency or the strength of the first electromagnetic signal MS1 based on the depth information DI. For example, the processing unit 323 of the control module 320 may receive the depth information DI and generate the control signal CS to adjust the frequency or amplitude of the AC signal AS based on the depth information DI to make the coil 312 generate the first electromagnetic signal MS1 of different frequencies and/or strengths. Alternatively, the first electromagnetic signal MS1 may be adjusted by using the control signal CS to adjust the electrical characteristics (for example, impedance value, inductance value, or capacitance value) of the sensor 310. However, the way to adjust the first electromagnetic signal MS1 is not limited thereto. On the other hand, the depth detection unit 340 may be a unit composed of detection elements capable of penetration (for example, penetrating skin, cloth, or other media) such as optical (the detection signal is an optical signal) or acoustic (the detection signal is an acoustic signal) elements. The depth detection unit 340 measures the depth of a blood vessel in a target area through a ranging mechanism such as time-of-flight ranging (TOF). However, the elements and mechanisms for measuring the depth information DI are not limited thereto.

The depth detection unit 340 may be arranged on or integrated with the substrate 311 to achieve better efficiency in determining the depth. Through the depth information DI provided by the depth detection unit 340, the control module 320 may select a better signal for measurement, thereby improving the energy transfer efficiency of the first electromagnetic signal MS1 and the second electromagnetic signal MS2, and the power consumption of the measuring device 300 for measuring the cardiopulmonary state can be reduced. Efficient energy transfer can also greatly reduce the risk of subjects being exposed to electromagnetic waves. On the other hand, based on the depth information DI, the first electromagnetic signal MS1 may also focus on a target depth by using a focusing method such as a phase array. In this way, better measurement quality and a better signal-to-noise ratio can be achieved.

Fourth Embodiment

Figure 8:
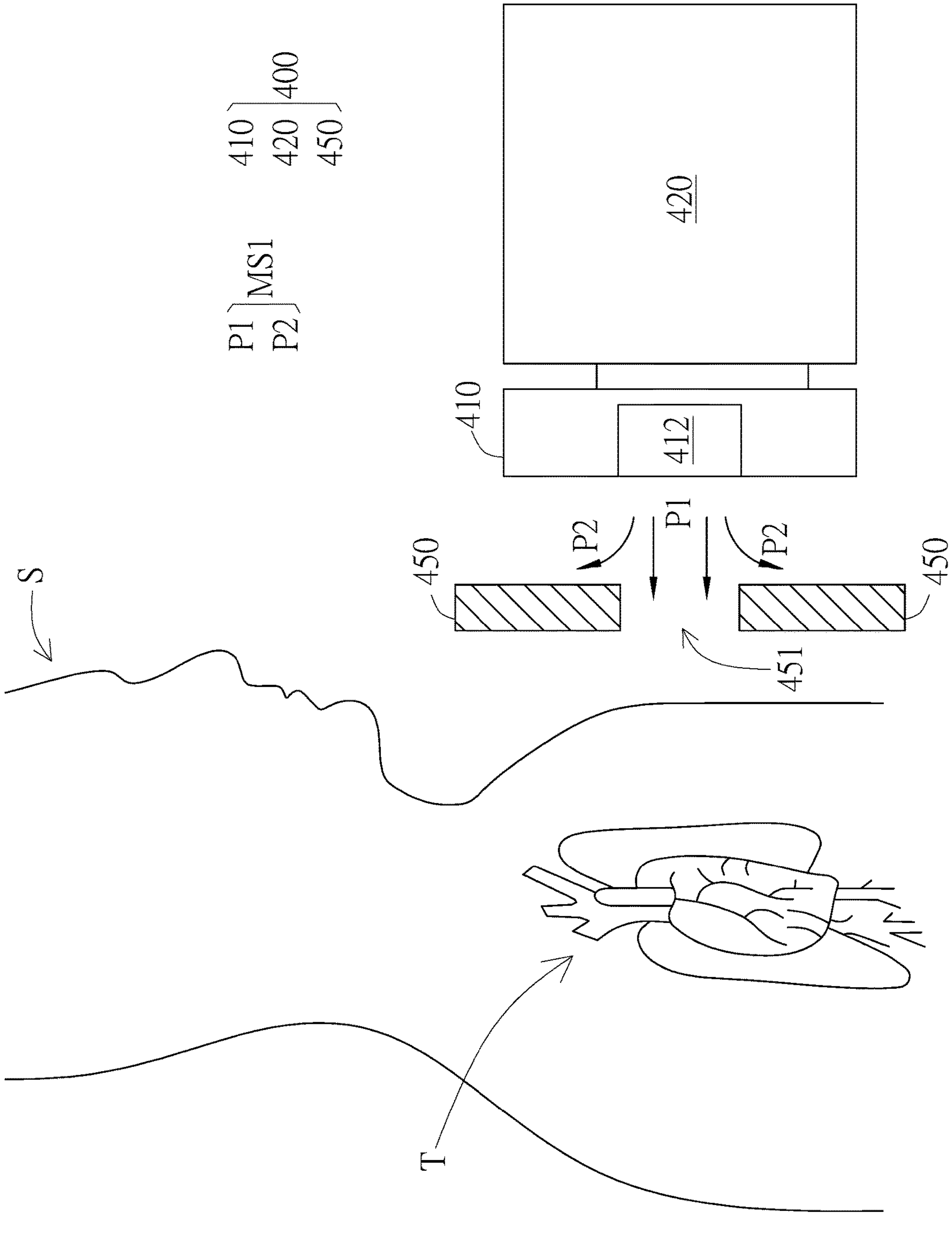
FIG. 8 is a schematic diagram of the measuring device having an isolation unit for measuring cardiopulmonary state according to the fourth embodiment of the present invention.

Referring to FIG. 8, the measuring device 400 for measuring the cardiopulmonary state also includes an isolation unit 450 arranged between the sensor 410 and the subject S. Wherein the isolation unit 450 has the gap 451 for passing a first portion P1 of the first electromagnetic signal MS1 toward the to-be-measured part T. Wherein the isolation unit 450 is configured to block a second portion P2 of the first electromagnetic signal MS1 to not pass the gap. In other words, the first portion P1 of the first electrical signal MS1 is not blocked by the isolation unit 450. The isolation unit 450 blocks the second portion P2 of the first electrical signal MS1. The second portion P2 of the first electrical signal MS1 is blocked by the isolation unit 450 and cannot pass through the gap 451.

The material of the isolation unit 450 may be selected from electrical conductors, magnetic conductors, or other material that can block electromagnetic waves. The first electrical signal MS1 is output from the coil 412 of the sensor 410 toward the to-be-tested part T. However, because of the divergence of magnetic field lines, the first electromagnetic signal MS1 has a divergent portion (the second portion P2) which does not point toward the to-be-tested part T. Therefore, the second portion P2 of the first electrical signal MS1 cannot fully (or cannot) work on the to-be-tested part T and may generate noise and affect the sensing signal. The generated noise may interfere with the non-divergent portion (i.e., the first portion P1) of the first electrical signal MS1 pointing towards the to-be-tested part T and/or the second electrical signal MS2 generated by the eddy current I. In this embodiment, through the gap 451 of the isolation unit 450, the first portion P1 of the first electrical signal MS1 will pass through the gap 451 without being blocked by the isolation unit 450, and the second portion P2 of the first electrical signal MS1 will be blocked by the isolation unit 450. By having the isolation unit 450, the signal-to-noise ratio can be raised. The shape or type of the gap 451 may be selected from, for example, circular, square, or other shapes based on the shape or configuration of the coil 412. It should be noted that the shape and/or arranging position of the gap 451 on the isolation unit 450 can be adjusted according to actual needs.

Fifth Embodiment

Figure 9:
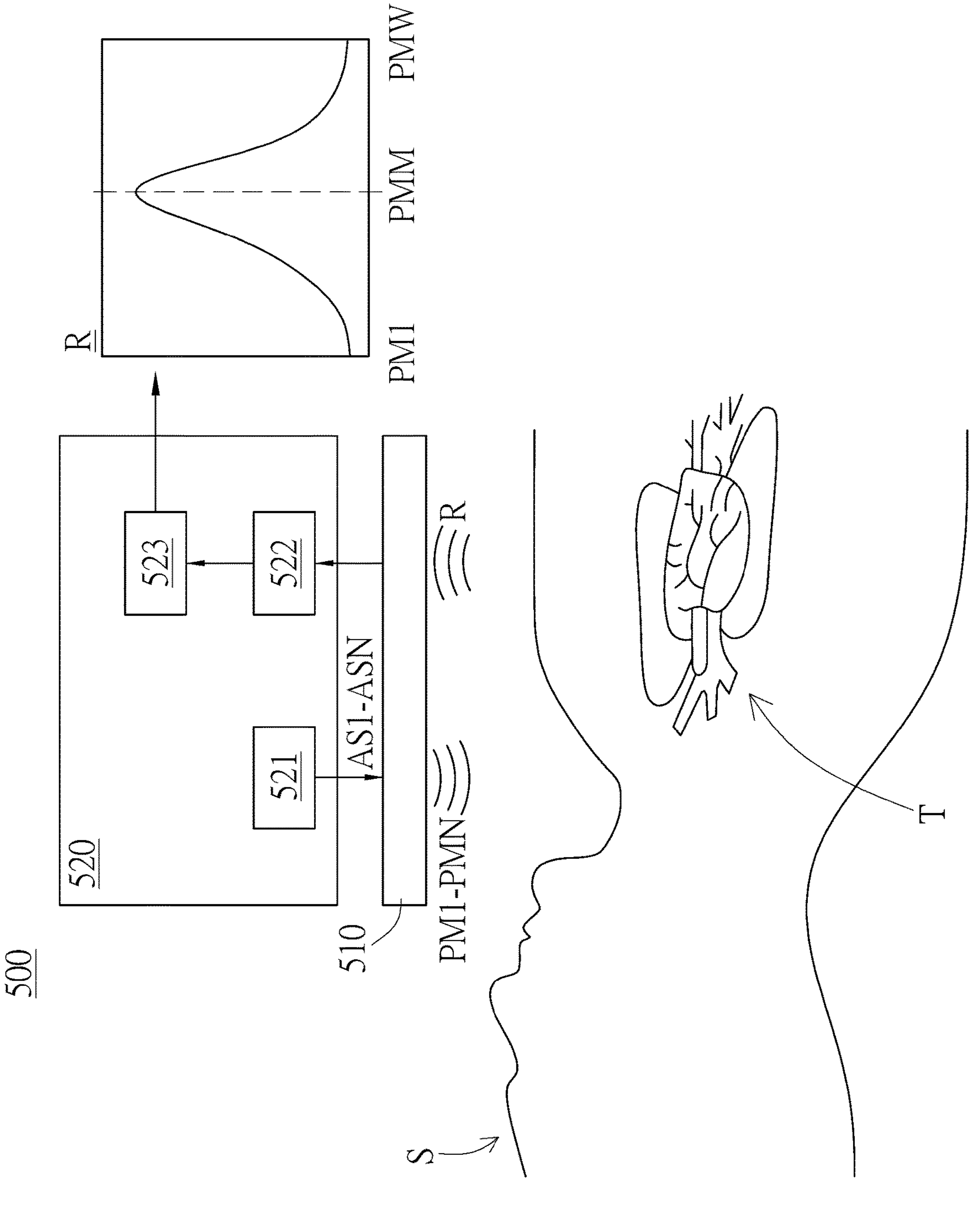
FIG. 9 to FIG. 11 are schematic diagrams of the measuring device outputting leading electromagnetic signals for measuring cardiopulmonary state according to the fifth embodiment of the present invention.

In this embodiment, as shown in FIG. 9, before outputting the first electromagnetic signal MS1, the signal transceiver 510 of the measuring device 500 for measuring cardiopulmonary state further outputs at least one leading electromagnetic signal PM1-PMN. Each of the leading electromagnetic signals PM1-PMN corresponds to a different signal parameter, and the signal parameter of the first electromagnetic signal MS1 corresponds to one of the leading electromagnetic signals PM1-PMN with the optimal response.

Specifically, the signal transceiver 510 generates the first electromagnetic signal MS1 based on the AC signal AS provided by the signal generation unit 521. However, different subjects or different to-be-measured parts may use different signal parameters (for example, frequency, amplitude, or strength) to obtain optimal/better measurement results. Therefore, before the signal transceiver 510 outputs the first electromagnetic signal MS1, at least one leading electromagnetic signal PM1-PMN is used for pre-scanning, thereby selecting the best or relatively better first electromagnetic signal MS1 for measurement.

In this embodiment, as shown in FIG. 9, the signal generation unit 521 may be configured to output at least one leading AC signal AS1-ASN to generate at least one leading electromagnetic signal PM1-PMN. Each of the leading electromagnetic signals PM1-PMN corresponds to one of the leading AC signals AS1-ASN. Specifically, the signal generation unit 521 outputs the leading AC signals AS1-

ASN of different frequencies in sequence (for example, in ascending or descending order of the frequencies) in a possible frequency interval (for example, kilohertz to megahertz). The leading electromagnetic signals PM1-PMN are then generated, and the frequencies of the leading electromagnetic signals PM1-PMN are different since they correspond respectively to the frequencies of the leading AC signals AS1-ASN. By scanning with the leading electromagnetic signals PM1-PMN of different frequencies, eddy currents I of different magnitudes may be generated at the to-be-measured part T, and corresponding responses of different magnitudes may be generated. For example, responsive electromagnetic signals of different strengths may be generated. The control module 520 may determine the frequency of the AC signal AS outputted by the signal generation unit 521 based on the transmission frequency (PMM) corresponding to the largest or best of the responses received by the signal transceiver 510 to generate the best or relatively better first electromagnetic signal MS1 for measurement.

Figure 10:
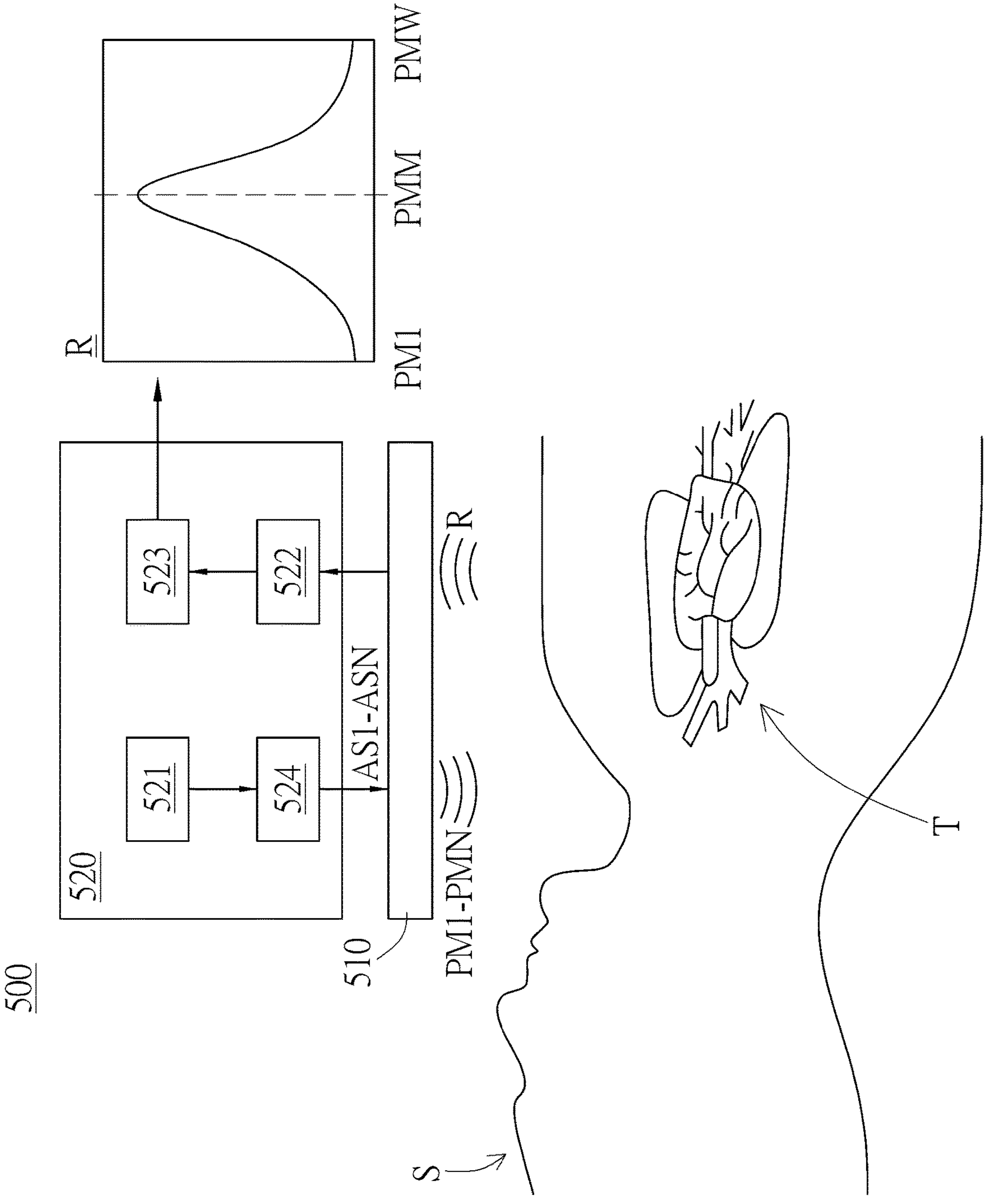

In this embodiment, another mechanism for regulating signal parameters is shown in FIG. 10. The control module 520 includes an adjustable passive element 524 coupled with the signal transceiver 510, and the control module 520 adjusts the capacitance value, inductance value, and/or impedance value of the adjustable passive element 524 to adjust the signal parameters of each of the leading electromagnetic signals PM1-PMN. Specifically, the adjustable passive element 524 is coupled with the signal transceiver 510, and the adjustable passive element 524 may be adjusted by, for example, an adjustable capacitor. The capacitance value of the adjustable capacitor may indirectly adjust the capacitance value and/or impedance value of the signal transceiver 510. Therefore, when the leading electromagnetic signals PM1-PMN are to be generated, the signal parameters of each of the leading electromagnetic signals PM1-PMN may be adjusted to be different by changing the capacitance value of the adjustable passive element 524 through the AC signal AS provided by the signal generation unit 521. Eddy currents of different magnitudes are then generated at the to-be-measured part T through the leading electromagnetic signals PM1-PMN, and responses of different magnitudes are correspondingly generated. Therefore, the best/relatively better capacitor value can be selected. It should be noted that the adjustable passive element 524 is not limited to the adjustment of capacitance value. An adjustable passive element 524 may be an element that is adjustable for at least one of the resistance value, the impedance value, the capacitance value, and/or the inductance value.

Figure 11:
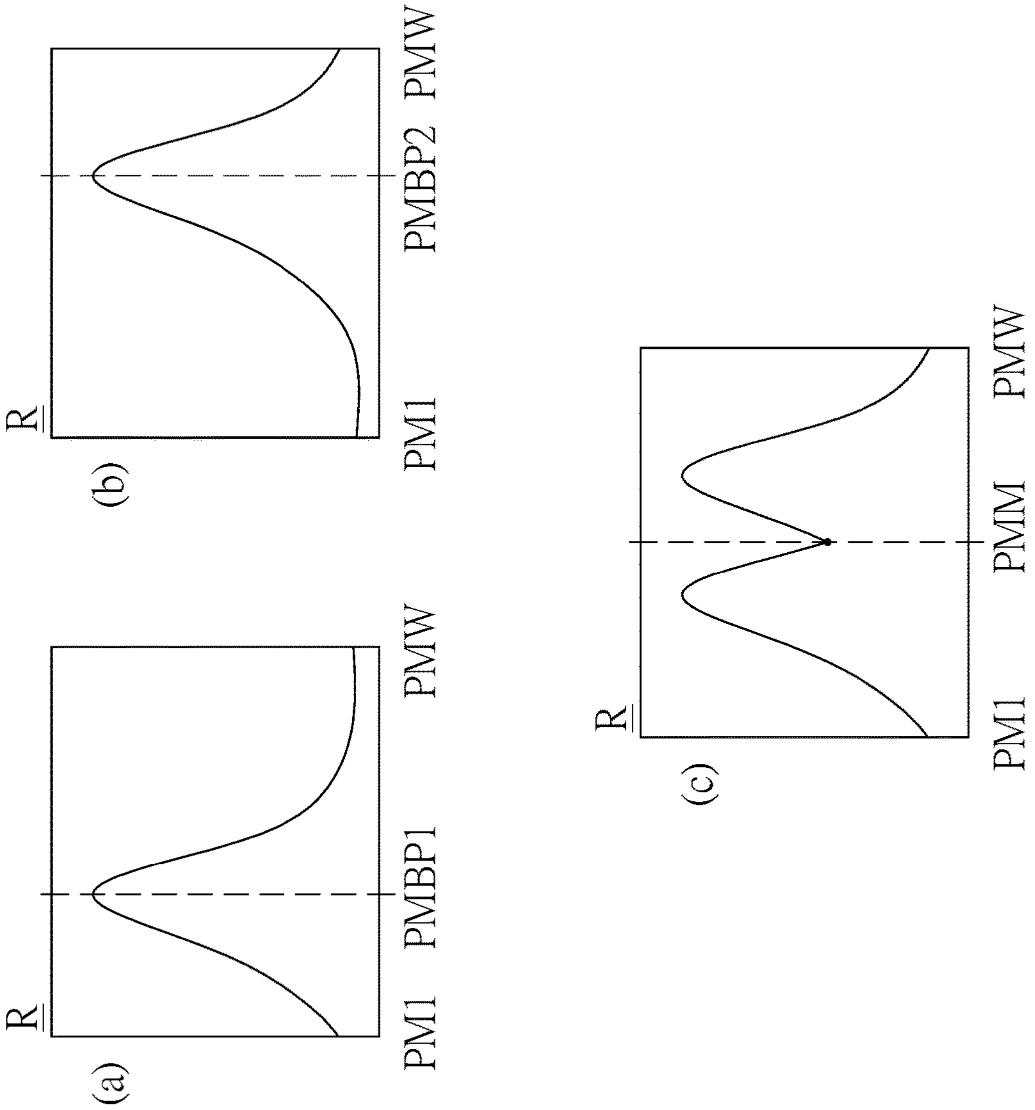

It should be noted that in the embodiment, while the first electrical signal MS1 with optimal or relatively optimal parameters/setting can be selected through the control module 520, it can also be determined based on the response amplitude of the first filter frequency band BP1 or the second filter frequency band BP2. For example, when focusing on the measurement of the first filter frequency band BP1, one of the leading electromagnetic signals PM1-PMN that corresponds to a larger response in the first filter frequency band BP1 (such as PMBP1 in FIG. 11 (*a*)) can be selected as the first electrical signal MS1. On the other hand, when focusing on the measurement of the second filter frequency band BP2, one of the leading electromagnetic signals PM1-PMN that corresponds to a larger response in the second filter frequency bandBP2 (such as PMBP2 in FIG. 11 (*b*)) can be selected as the first electrical signal MS1. However, a compromise can also be made by selecting from the leading electromagnetic signals PM1-PMN a signal that has a relatively large response to the first filter frequency band BP1 and the second filter frequency band BP2 (such as the PMM in FIG. 11 (*c*)) as the first electromagnetic signal MS1.

Through the leading electromagnetic signals PM1-PMN, the measuring device 500 may be calibrated before measurement, so that the measurement parameters most suitable for the subject or the tested part can be generated. In this way, measurement errors caused by the subject or the tested part can be avoided. In addition, selecting preferable measurement parameters can also improve measurement efficiency, reduce power consumption of the measuring device 500, and lower the risk of electromagnetic waves.

Sixth Embodiment

Figure 12:
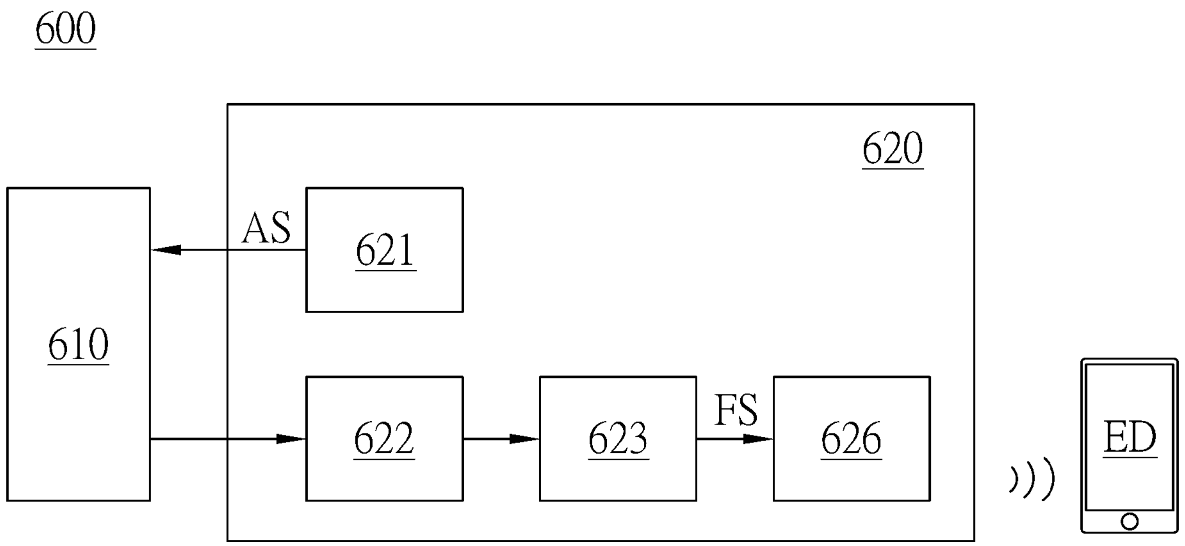
FIG. 12 is a schematic diagram of the measuring device having a communication unit for measuring cardiopulmonary state according to a fourth embodiment of the present invention.

In this embodiment, as shown in FIG. 12, the device 600 for measuring cardiopulmonary state comprises the control module 620 which has a communication unit 626. The communication unit 626 is coupled with a processing unit 623 and configured to output at least one feature signal FS1-FSN to an electronic device ED. Specifically, the electronic device ED is, for example, a back-end device such as a smart phone, a desktop computer, or a notebook computer. The communication unit 626 communicates with the electronic device ED in a wireless (for example, Bluetooth, wireless network, infrared ray, etc.) or wired (for example, wired network or cable) manner and provides at least one feature signal FS1-FSN to the electronic device ED. An application program may be installed in the electronic device ED to record or analyze the feature signal FS. Therefore, the purpose of tracking or evaluating the heart/lung state can be achieved, but not limited thereto.

The previous description of the present invention is provided to enable a person of ordinary skill in the art to make or implement the present invention. Various modifications to the present invention will be apparent to a person skilled in the art, and the general principles defined herein can be applied to other variations without departing from the spirit or scope of the present invention. Therefore, the present invention is not intended to be limited to the examples described herein, but is to be in accord with the widest scope consistent with the principles and novel features of the invention herein.

What is claimed is:

1. A device for measuring cardiopulmonary state, the device comprising:

a sensor including:

- a substrate;
- a coil arranged on the substrate, the coil configured to transmit a first electromagnetic signal toward a to-be-measured part of a subject, and at least receive a second electromagnetic signal generated at the to-be-measured part induced by the first electromagnetic signal, wherein the second electromagnetic signal is converted to a sensing signal by the coil; and a control module including:

- a signal generation unit coupled to the coil, wherein the signal generation unit is configured to generate an AC signal provided to the coil to generate the first electromagnetic signal;
- a filter unit coupled to the coil at least having a first filter frequency band and a second filter frequency band, and configured to filter the sensing signal into a first portion corresponding to the first filter frequency band, and a second portion corresponding to the second filter frequency band; and a processing unit coupled to the filter unit, wherein the processing unit is configured to calculate, based on the first portion and the second portion, at least one feature signal of the subject's cardiopulmonary state;

wherein prior to outputting the first electromagnetic signal, the sensor further outputs at least one leading electromagnetic signal; and wherein each of the at least one leading electromagnetic signal corresponds to a different signal parameter, the signal parameter of the first electromagnetic signal corresponds to one of the at least one leading electromagnetic signal having an optimal response.

2. The measuring device of claim 1, wherein the filter unit includes a first band-pass filter and a second band-pass filter; and wherein the passband of the first band-pass filter corresponds to the first filter frequency band, and the passband of the second band-pass filter corresponds to the second filter frequency band.

3. The measuring device of claim 1, wherein the first filter frequency band is at least partially lower than the second filter frequency band.

4. The measuring device of claim 3, wherein the processing unit calculates, based on the first portion, a first feature signal of the subject's pulmonary state.

5. The measuring device of claim 3, wherein the processing unit calculates, based on the second portion, a second feature signal of the subject's cardiac state.

6. The measuring device of claim 1, wherein the signal generation unit outputs at least one leading AC signal to generate the at least one leading electromagnetic signal, and each of the at least one leading electromagnetic signal corresponds to one of the at least one leading AC signal.

7. The measuring device of claim 1, further comprising an adjustable passive element coupled to the coil and arranged on at least one of the substrate and the control module, wherein the control module adjusts the adjustable passive element to adjust a signal parameter of each of the at least one leading electromagnetic signal.

8. The measuring device of claim 1, further comprising:

an isolation unit arranged between the sensor and the subject; wherein the isolation unit has a gap for passing a third portion of the first electromagnetic signal toward the to-be-measured part; wherein the isolation unit is configured to block a fourth portion of the first electromagnetic signal, which does not pass through the gap.

9. The measuring device of claim 1, wherein the control module further includes:

a communication unit coupled to the processing unit and configured to transmit the at least one feature signal to an electronic device.

10. The measuring device of claim 1, wherein the control module is arranged on the substrate.

11. The measuring device of claim 1, wherein the signal generation unit includes a DC power supplier and a resonant circuit; wherein the resonant circuit is configured to receive a DC signal provided by the DC power supplier and generate the AC signal.

* * * * *